US010500200B2

(12) United States Patent
Giesing

(10) Patent No.: US 10,500,200 B2
(45) Date of Patent: Dec. 10, 2019

(54) DRUG DELIVERY SYSTEMS AND METHODS FOR TREATMENT OF BLADDER DYSFUNCTION OR DISORDER USING TROSPIUM

(71) Applicant: TARIS Biomedical LLC, Lexington, MA (US)

(72) Inventor: Dennis Giesing, Lee's Summit, MO (US)

(73) Assignee: TARIS Biomedical LLC, Lexington, MA (US)

( * ) Notice: Subject to any disclaimer, the term of this patent is extended or adjusted under 35 U.S.C. 154(b) by 0 days.

(21) Appl. No.: 14/658,699

(22) Filed: Mar. 16, 2015

(65) Prior Publication Data

US 2015/0182516 A1   Jul. 2, 2015

Related U.S. Application Data

(63) Continuation of application No. PCT/US2013/060479, filed on Sep. 18, 2013.

(60) Provisional application No. 61/702,576, filed on Sep. 18, 2012.

(51) Int. Cl.
*A61K 31/46* (2006.01)
*A61K 9/00* (2006.01)
*A61M 31/00* (2006.01)

(52) U.S. Cl.
CPC ............ *A61K 31/46* (2013.01); *A61K 9/0034* (2013.01); *A61M 31/002* (2013.01)

(58) Field of Classification Search
USPC ........................................................ 424/430
See application file for complete search history.

(56) References Cited

U.S. PATENT DOCUMENTS

| | | |
|---|---|---|
| 5,998,430 A | 12/1999 | Schwantes et al. |
| 8,343,516 B2 | 1/2013 | Daniel et al. |
| 8,679,094 B2 | 3/2014 | Cima et al. |
| 8,690,840 B2 | 4/2014 | Lee et al. |
| 8,801,694 B2 | 8/2014 | Lee et al. |
| 9,017,312 B2 | 4/2015 | Lee et al. |
| 2006/0154951 A1 | 7/2006 | Wood |
| 2007/0202151 A1* | 8/2007 | Lee et al. .................. 424/426 |
| 2009/0149833 A1 | 6/2009 | Cima et al. |
| 2010/0331770 A1 | 12/2010 | Lee et al. |
| 2011/0060309 A1* | 3/2011 | Lee et al. .................. 604/500 |
| 2011/0152839 A1* | 6/2011 | Cima et al. ................ 604/517 |
| 2012/0191068 A1 | 7/2012 | Himes et al. |
| 2012/0203203 A1 | 8/2012 | Lee et al. |
| 2013/0324946 A1 | 12/2013 | Tobias et al. |
| 2014/0276636 A1 | 9/2014 | Lee et al. |

FOREIGN PATENT DOCUMENTS

| | | |
|---|---|---|
| EP | 1632229 B1 | 1/2009 |
| WO | 2004052440 A1 | 6/2004 |
| WO | 2006101954 A2 | 9/2006 |

OTHER PUBLICATIONS

Tyagi (Chapter 10 of The Overactive Bladder: Evaluation and Management, Kreder and Dmochowski, editors, CRC Press; Jul. 10, 2007, pp. 115-124).*
Amend (European Urology 53 ( 2 0 0 8) 1021-1028).*
Onur (Urology 75 (4), 2010, pp. 873-877).*
International Search Report of PCT/US2013/060479 dated Nov. 2, 2014.
Andersson, et al. "Pharmacologic Management of Lower Urinary Tract Storage and Emptying Failure", Chapter 68, pp. 1967-2002.
Michaeli et al. "Development of an Active Agent Carrying, Biodegradable Implant for the Intravesical Therapy of the Overactive Bladder Syndrome", Annual Techn Conf. ANTEC, Confer Proceed, 5, 2951-56 (2009).
Grosse, et al.,"Release of Trospium Chloride from Expanded PLGA Carriers as Intravesical Drug Delivery", J. Urology 181(4): 571 (Suppl.); 1590, Apr. 28, 2009.
Von Walter, et al., Trospium Chloride Released from Intravesically Applied PLGA-Based Carriers Decreases Bladder Contractility in an Isolated Whole Pig Bladder Model: 230, Eur. Urol. Suppl. 2009; 8(4): 178.
Wiedemann & Schwantes, "Antimuscarinic Drugs for the Treatment of Overactive Bladder: Are they Really all the Same?—A Comparative Review of Data Pertaining to Pharmacological and Physiological Aspects", European Journal of Geriatrics (2007) Suppl. 1.
Ausgabe A., Urologe, vol. 50, Supp. 1, p. 88 Abstract No. P2.7, (abstract), Sep. 2011 (1 page).
Fröhlich, Gert "Intravesical Application of Trospium Chloride, Oxybutynin and Verapamil for Relaxation of the Urinary Bladder Detrusor Muscle", Arzneim.Forsch./Drug Res.48(I), 486-491 (1998) (6 pages).
Walter, P. "Bioavailability of Trospium Chloride After Intravesical Instillation in Patients With Neurogenic Lower Urinary Tract Dysfunction: A Pilot Study", Neurourology and Urodynamics 18:447-453 (1999) (7 pages).

* cited by examiner

*Primary Examiner* — Devang K Thakor
(74) *Attorney, Agent, or Firm* — Eversheds Sutherland (US) LLP

(57) ABSTRACT

Methods, devices, and medicaments that include trospium are provided for use in the treatment of bladder dysfunction by locally administering the trospium into the bladder to achieve a sustained concentration of trospium in urine in the bladder sufficient to produce a therapeutic concentration of trospium in bladder tissue. The drug may be delivered into the bladder from an intravesical drug delivery device inserted into the bladder, wherein the device continuously releases the drug into the urine in the bladder over an extended period of hours or days.

7 Claims, 10 Drawing Sheets

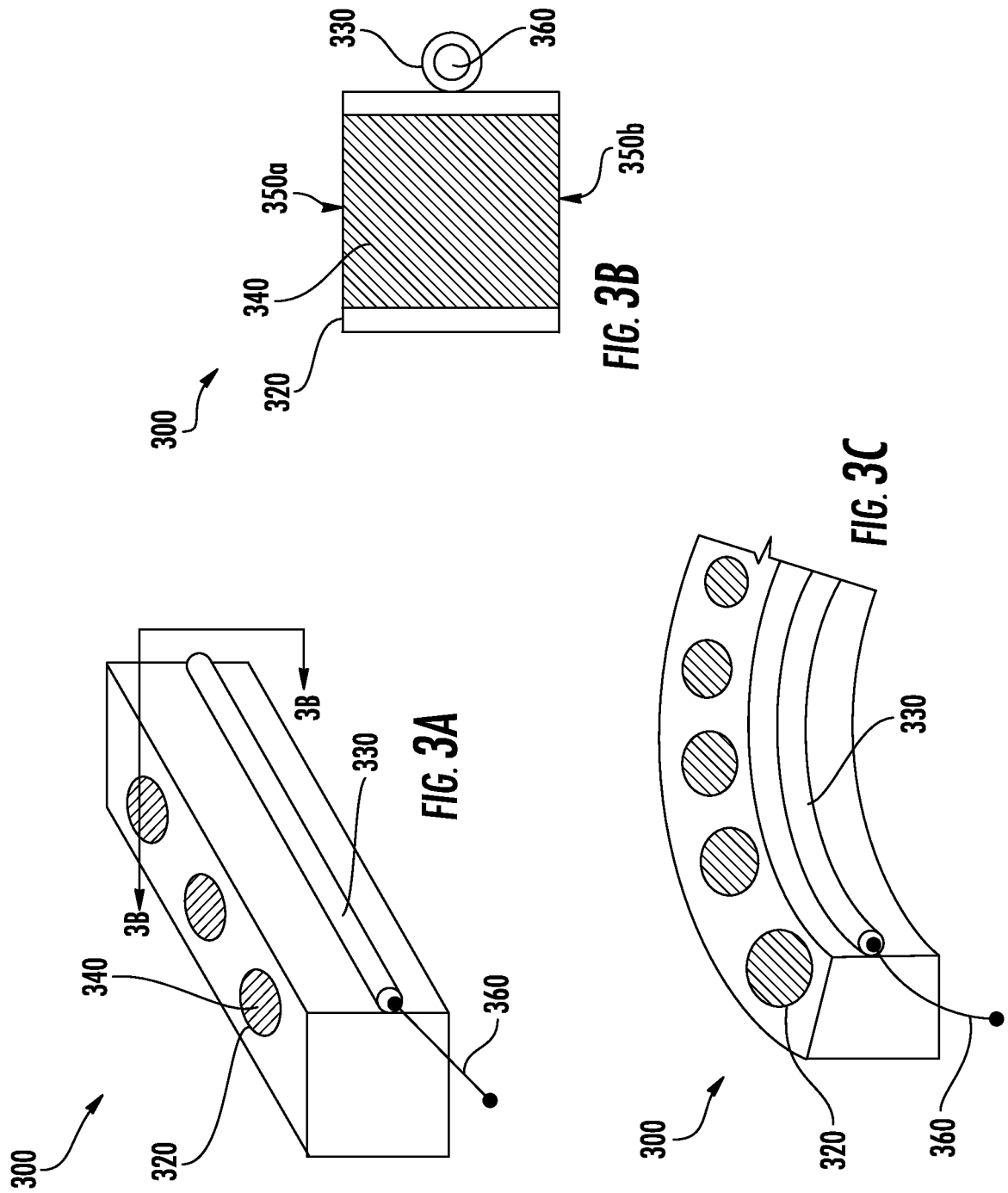

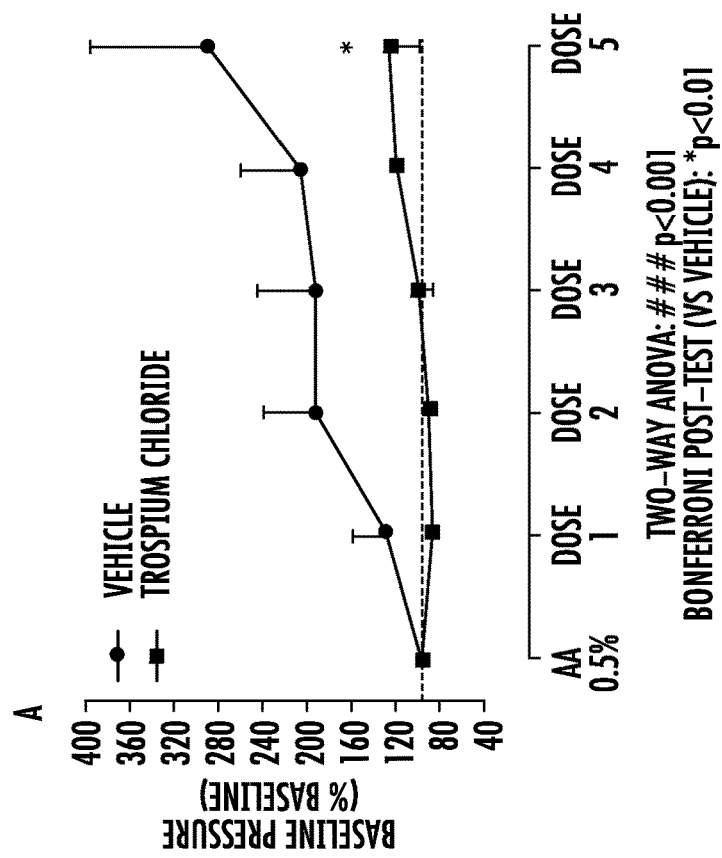
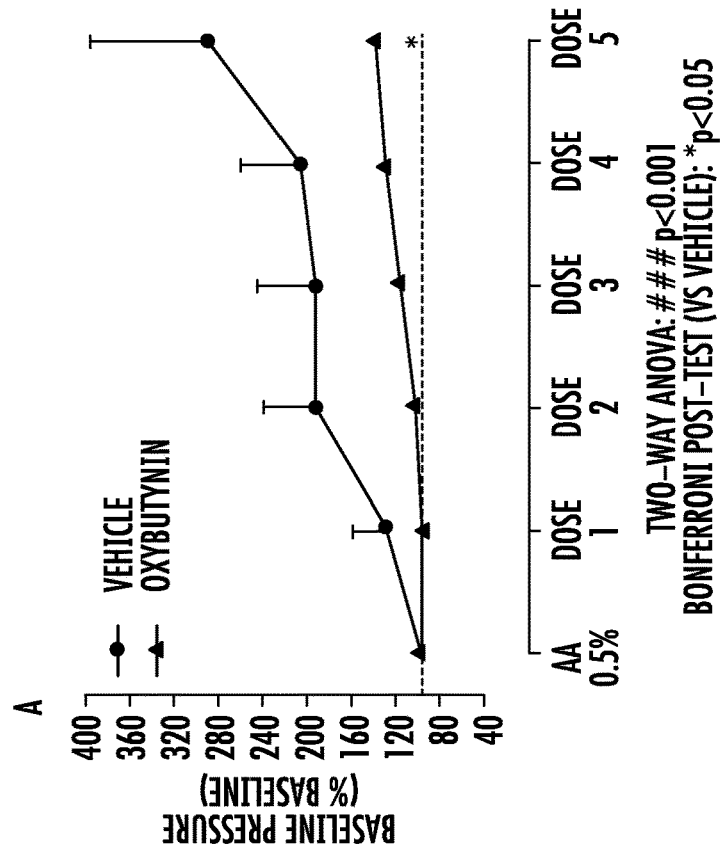
FIG. 7A
FIG. 7B

DRUG DELIVERY SYSTEMS AND METHODS FOR TREATMENT OF BLADDER DYSFUNCTION OR DISORDER USING TROSPIUM

CROSS-REFERENCE TO RELATED APPLICATIONS

This application is a continuation of PCT/US2013/060479, filed 18 Sep. 2013, which claims priority to U.S. Provisional Patent Application No. 61/702,576, filed Sep. 18, 2012, which is incorporated herein by reference in its entirety.

BACKGROUND

Lower urinary tract disorders, including overactive bladder, detrusor instability, and urinary incontinence can arise from numerous pathologies. These pathologies are commonly classified as neuropathic, myogenic, or idiopathic. The majority of patients usually are characterized as idiopathic due to the lack of observable disease etiology.

Recent studies (Kim, et al., Urology, 65(2):238-42 (2005); Kim, et al., BJU Int'l, 97(2):400-03 (2005)) have suggested the sensory system of the urothelium may play an important role in afferent signaling and detrusor activity. Pathologies of this system have been suggested to play a significant role in many patients with lower urinary tract idiopathic disease.

Standard drug therapies for patients with idiopathic lower urinary tract disorders are systemic treatments typically administered orally or trans-dermally. These therapies often lack adequate efficacy due to either dose limiting side effects, low potency, or both.

Currently patients failing systemic drug therapy have only two alternatives. The first alternative is Botox injections directly into the bladder wall, which may provide symptom relief, but which also undesirably can produce prolonged urinary retention requiring self-catheterization. The second alternative is neurosacral stimulation as produced by the InterStim® device which is surgically implanted and shown to provide symptomatic relief. However, the equipment and surgical procedure is expensive, highly invasive, and carries a 30% adverse event rate requiring corrective surgeries or removals.

Recent studies have suggested that intravesical administration of anti-muscarinic agents produces a different pharmacological response compared to systemic therapy (Kim, et al., Urology, 65(2):238-42 (2005); Kim, et al., BJU Int'l, 97(2):400-03 (2005)). These results have been primarily based on animal studies in which muscarinic agonists, for example carbachol, are used to stimulate urothelial activity to mimic sensory dysfunction.

In one of these studies (Kim, et al. Urology, 65(2):238-42 (2005)), antimuscarinic agents were instilled intravesically in two protocols—high dose and low dose. For the high dose (167 µg/mL) protocol, 300 µM atropine sulfate, 420 µM oxybutynin chloride, 410 µM dimethindene maleate were administered. These doses, except for dimethindene, were based on reported clinical trials that intravesically instilled these agents. Dimethindene was used for experimental purposes only. For the low dose (0.1 and 0.5 µg/mL) protocol, dimethindene, oxybutynin, tolterodine, and trospium were administered. These doses—0.1 and 0.5 µg/mL—were based on the excreted urine concentration of trospium in humans after receiving a steady-state oral dose of 40 mg/24 hours.

Based on carbachol antagonism (carbachol 30 µM ($M_1$, $M_2$, $M_3$, $AChRa_2$ agonist)), this study suggested that there are no significant differences among antimuscarinics when administered intravesically despite differences in chemical structure, muscarinic receptor selectivity, and potency. Within the low dose protocol, the intercontraction interval ratio to baseline data revealed that dimethindene, oxybutynin, tolterodine, and trospium all performed similarly.

In a related study (Kim, et al., BJU Int'l, 97(2):400-03 (2005)), human volunteers collected urine after taking oral therapeutic doses of trospium (20 mg, twice daily), tolterodine LA (4 mg, once daily), or oxybutynin XL (10 mg, once daily) for 5 days. The human urine was then infused into the bladders of rats to test the effects of antimuscarinics excreted into the urine on normal bladder activity. Although the data indicated that trospium had a more positive effect on bladder capacity and intercontraction interval than oxybutynin and tolterodine, this discrepancy was caused by the fact that 60-80% of the active parent compound of trospium chloride was excreted in the human's urine while <5% of the active compound of oxybutynin or tolterodine was excreted in the human's urine.

The urothelial sensory system is comprised of numerous receptors and signaling pathways, many of which exhibit significant "cross talk." Due to the complexity of the urothelial sensory system, selective agents, such as darifenasin, may not adequately modulate urothelial sensory activation following nonspecific noxious stimuli. Similarly, non-specific agents, such as oxybutynin which exhibits antimuscarinic and calcium channel activity, do not inhibit urothelial response as measured by intercontraction intervals but can lead to urinary retention.

Accordingly, there remains a need for more and better treatment options for lower urinary tract disorders, including overactive bladder, detrusor instability, and urinary incontinence. Desirably, such treatments would address one or more of the problems associated with systemic administration of drugs and with highly invasive and expensive surgical procedures. Desirably, the treatment would also avoid or lessen the need for painful injections and repeated self-catheterization.

BRIEF SUMMARY

In one aspect, a medicament is provided which includes trospium for use in the treatment of bladder dysfunction by locally administering the trospium into the bladder of a patient to achieve a sustained concentration of trospium in urine in the bladder sufficient to produce a therapeutic concentration of trospium in bladder tissue. In embodiments of the medicament, the trospium is in the form of trospium chloride or another pharmaceutically acceptable salt of trospium. The locally administering into the patient's bladder is at a mean average amount of from 0.075 mg/day to about 150 mg/day of trospium for a treatment period of up to 180 days. In an embodiment, the locally administering into the patient's bladder is at a mean average amount of 0.15 mg/day to 15 mg/day of trospium. In some embodiments, the treatment period is from 1 day to 90 days or from 1 day to 60 days.

In a particular embodiment, the trospium is delivered into the bladder from an intravesical drug delivery device which releases trospium into the urine in the bladder over the treatment period. The device may release the trospium continuously over the period. In one embodiment, the intravesical drug delivery device includes a housing which contains and controllably releases the trospium and which is elastically deformable between a retention shape configured to retain the device in a patient's bladder and a deployment shape for passage of the device through the patient's urethra. The trospium contained in the housing may be in a non-liquid form, such as tablets, granules, semisolids, capsules, or combinations thereof.

In another embodiment, the trospium is delivered to the bladder from a coating substance, such as a mucoadhesive formulation, applied onto the bladder wall, wherein the coating substance continuously releases trospium into the urine in the bladder over a sustained period. In still another embodiment, the step of locally administering includes pumping a liquid form of the trospium into the bladder through a urethral catheter which is deployed into the bladder.

In another aspect, a method is provided for administering trospium to a patient in need of treatment of bladder dysfunction. The method includes locally administering trospium into the bladder of a patient to achieve a sustained concentration of trospium in urine in the bladder sufficient to produce a therapeutic concentration of trospium in bladder tissue. The method may further include administering a second therapeutic agent to the patient. The second therapeutic agent may also be administered intravesically or it may be administered by other routes.

In yet another aspect, a drug delivery device is provided which is configured to release trospium when the drug delivery device is inserted into the bladder. In one embodiment, the device includes a housing configured for intravesical insertion, and a dosage form which comprises a pharmaceutically acceptable salt of trospium, wherein the housing holds the dosage form and is configured to release the trospium into the bladder in amount therapeutically effective for the treatment of bladder dysfunction. In one embodiment, the device is configured to release a mean average amount of from 0.075 mg/day to about 150 mg/day of trospium for a treatment period of up to 180 days. For example, the device may be configured to release at a mean average amount of 0.15 mg/day to 15 mg/day of trospium. In some embodiments, the treatment period is from 1 day to 90 days or from 1 day to 60 days.

In embodiments, the bladder dysfunction is selected from urinary frequency, urgency, nocturia, urge-incontinence associated with detrusor instability, urge syndrome, and detrusor hyperreflexia.

BRIEF DESCRIPTION OF THE DRAWINGS

FIGS. 3A-3C illustrate still another embodiment of an intravesical drug delivery device that may be used for administering trospium as described herein.

FIGS. 7A-7F illustrate the baseline pressure and intercontraction intervals observed after administering tolterodine, oxaliplatin, and trospium.

DETAILED DESCRIPTION

Figure 1A:
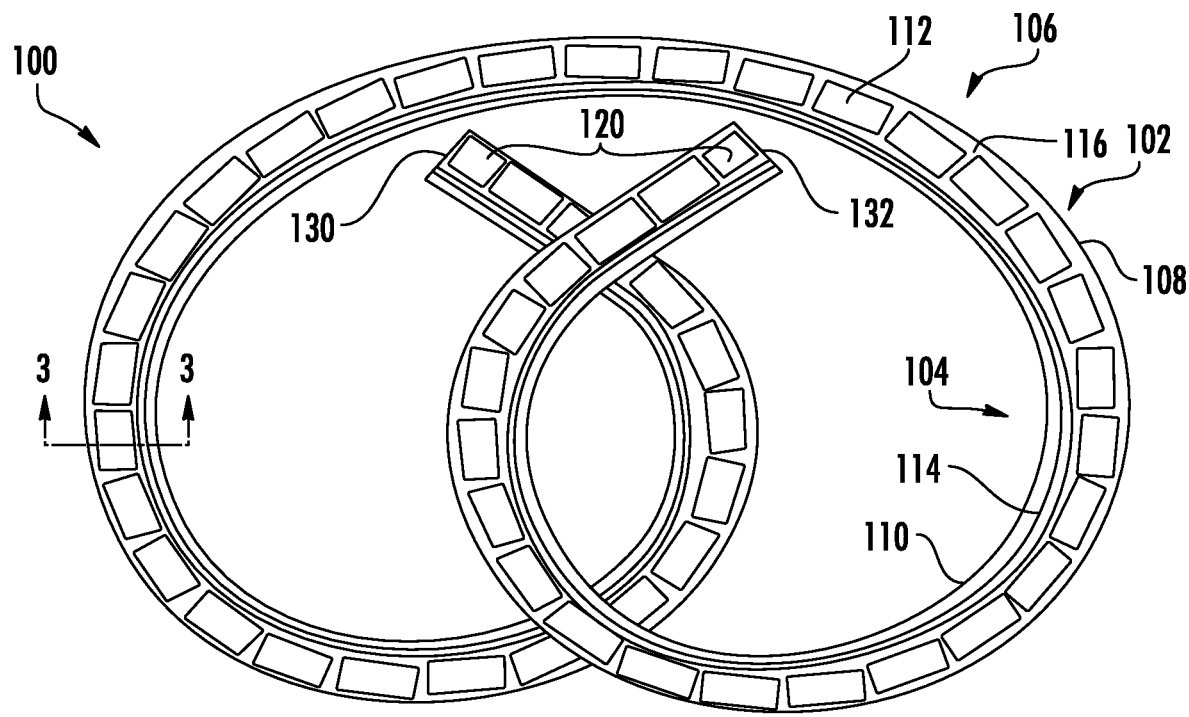
FIGS. 1A-1B illustrate one embodiment of an intravesical drug delivery device that may be used for administering trospium as described herein.

Trospium has been discovered to uniquely effect both detrusor activity and urothelium sensory function as measured by intercontraction interval when administered intravesically. In contrast, comparator agents such as oxybutynin and tolterodine only impact detrusor activity. Intercontraction interval is a measure of the time between bladder contractions (which may or may not lead to micturition). The frequency of these contractions is a measure of urothelial sensory signaling activity. The unique property of trospium on urothelial sensory function when administered intravesically advantageously limits systemic exposure and adverse effects.

Although previous studies have shown no substantial differences among trospium, oxybutynin, and tolterodine, it has now been discovered that trospium does exhibit a unique urodynamic profile when administered intravesically. As detailed in Example 2 below, this was observed when a noxious agent, for example acetic acid, is exposed to the urothelium which produces a generalized local irritation that is more representative of actual lower urinary disease conditions. Specifically, trospium was observed to increase intercontraction interval, a measure of urothelial sensory activity, at or below intravesical concentrations of commonly used agents including oxybutynin and tolterodine, neither of which altered intercontraction interval. Further, unlike oxybutynin, which is a nonspecific agent, interacting with both muscarinic and non-muscarinic receptors, trospium exhibited normalized urothelial sensory function at intravesical concentration that did not produce urinary retention or significant systemic exposure.

Urothelial sensory dysfunction may also cause symptoms of urinary urgency in patients with interstitial cystitis and urethra dysfunction (pelvic floor dysfunction, urethral dysfunction). Accordingly, intravesical trospium may also have use in treating a variety of lower urinary tract disorders. In various embodiments, trospium is used to treat one or more of the following conditions: urinary frequency, urgency, nocturia, urge-incontinence associated with detrusor instability, urge syndrome, and detrusor hyperreflexia.

Trospium is a muscarinic receptor antagonist. It is known for use in the treatment of overactive bladder, where it is formulated for oral administration, e.g., Sanctura™ (Allergan). As with other oral muscarinic receptor antagonists, patients often experience dose limiting side effects or inadequate efficacy. In the present invention, the trospium is formulated for local delivery. It may be provided in solid or semi-solid form or in a liquid form, depending on the delivery mechanism employed, as described herein. In a preferred embodiment of the methods, devices, and systems described herein, the trospium is provided in the form of a pharmaceutically acceptable salt of trospium. In a particular embodiment, the pharmaceutically acceptable salt of trospium is trospium chloride. Other suitable forms of trospium are also envisioned, including but not limited to polymorphs, hydrates, etc.

A variety of methods can be used to achieve the required urine concentrations of the drug. In one embodiment, the drug can be provided by direct instillation of a simple solution into the bladder. For example, a solution of the drug may be pumped into the bladder through a urethral or suprapubic catheter in a continuous or pulsatile manner over the treatment period. In another embodiment, the drug is released from a device or composition deployed in the bladder, wherein the device or composition releases the drug (continuously or intermittently) at a rate effective to produce the desired concentration of drug in the urine over a specified treatment period. For example, the drug may be released from an intravesically-inserted device into the bladder and then the drug diffuses to drug receptors located at the luminal wall of the urothelium and throughout the bladder wall. At the end of the treatment period, the device may be retrieved from the bladder, or it may be eliminated by being resorbed, dissolved, excreted, or a combination thereof.

In a preferred embodiment, the drug is administered from an intravesically deployed drug delivery device. Preferred examples of intravesical drug delivery devices and methods of deploying those devices into the bladder are described in the following U.S. Patent Application Publications: US 2012/0203203 (Lee et al.); US 2012/0089122 (Lee et al.); US 2012/0089121 (Lee et al.); US 2011/0218488 (Boyko et al.); US 2011/0202036 (Boyko et al.); US 2011/0152839 (Cima et al.); US 2011/0060309 (Lee et al.); US 2010/0331770 (Lee et al.); US 2010/0330149 (Daniel et al.); US 2010/0003297 (Tobias et al.); US 2009/0149833 (Cima et al.); and US 2007/0202151 (Lee et al.).

In embodiments in which the trospium is delivered from an intravesical drug delivery device, the drug may be housed in the device in various forms, which may depend on the particular mechanism by which the device controllably releases the drug into fluid (e.g., urine) in the bladder. In some embodiments, the drug is provided in a solid, semi-solid, or other non-liquid form, which advantageously may facilitate stable storage of the drug before the device is used and advantageously may enable the drug payload of the device to be stored in smaller volume than would be possible if the drug were housed in the form of a liquid solution. In an embodiment, the non-liquid form is selected from tablets, granules, semisolids, capsules, and combinations thereof. In one embodiment, the trospium is in the form of a plurality of tablets, such as mini-tablets. In other embodiments, the drug may be housed in a liquid form, such as in a solution with a pharmaceutically acceptable excipient.

An embodiment of a drug delivery device 100 is illustrated in FIG. 1A. The device 100 includes a water-permeable body having a drug reservoir portion 102 and a retention frame portion 104. In FIG. 1, the device 100 is shown in a relatively expanded shape suited for retention in the body. Following deployment into the body, the device 100 may assume the relatively expanded shape to retain the drug delivery device in the body cavity or lumen.

For the purposes of this disclosure, terms such as "relatively expanded shape", "relatively higher-profile shape", or "retention shape" generally denote any shape suited for retaining the device in the intended implantation location, including but not limited to the pretzel shape shown in FIG. 1 that is suited for retaining the device in the bladder. Similarly, terms such as "relatively lower-profile shape" or "deployment shape" generally denote any shape suited for deploying the drug delivery device into the body, including a linear or elongated shape that is suited for deploying the device through the working channel of catheter, cystoscope, or other deployment instrument positioned in the urethra. In embodiments, the drug delivery device may naturally assume the relatively expanded shape and may be deformed, either manually or with the aid of an external apparatus, into the relatively lower-profile shape for insertion into the body. Once deployed the device may spontaneously or naturally return to the initial, relatively expanded shape for retention in the body.

In the illustrated embodiment, the drug reservoir and retention frame portions 102, 104 of the drug delivery device 100 are longitudinally aligned and are coupled to each other along their length, although other configurations are possible. The drug delivery device 100 includes an elastic or flexible device body 106 that defines a drug reservoir lumen 108 (i.e., the drug housing) and a retention frame lumen 110. The drug reservoir lumen 108 is designed to house a drug formulation, such as a number of solid drug tablets 112. The retention frame lumen 110 is designed to house a retention frame 114 to form the retention frame portion 104. The illustrated lumens 108, 110 are discrete from each other, although other configurations are possible.

Figure 1B:
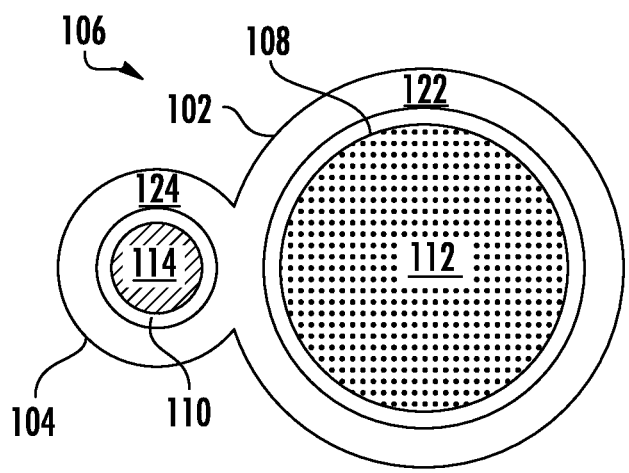

As shown in the cross-sectional view of FIG. 1B, the device body 106 includes a tube or wall 122 that defines the drug reservoir lumen 108 and a tube or wall 124 that defines the retention frame lumen 110. The tubes 122, 124 and lumens 108, 110 can be substantially cylindrical, with the drug reservoir lumen 108 having a relatively larger diameter than the retention frame lumen 110, although other configurations can be selected based on, for example, the amount of drug to be delivered, the diameter of the retention frame, and deployment considerations such as the inner diameter of the deployment instrument. The wall 124 that defines the retention frame lumen 110 may extend along the entire length of the wall 122 that defines the drug reservoir lumen 108, so that the retention frame lumen 110 has the same length as the drug reservoir lumen 108 as shown, although one wall may be shorter than the other wall in other embodiments. The two walls 122, 124 are attached along the entire length of the device in the illustrated embodiment, although intermittent attachment can be employed.

As shown in FIG. 1A, the drug reservoir lumen 108 is loaded with a number of drug units 112 in a serial arrangement. Essentially any number of drug units may be used, for example, depending upon the sizes of the reservoir and the drug units. The drug reservoir lumen 108 includes a first end opening 130 and an opposed second end opening 132. Once the drug units 112 are loaded, restraining plugs 120 are disposed in the openings 130 and 132. The restraining plugs 120, in this embodiment, are cylindrical plugs secured into opening 130 and opening 132. In other embodiments, the openings 130 and 132 are closed off with other structures or materials, which may, depending on the particular embodiments, include an aperture or a water- or drug-permeable wall to facilitate ingress or egress of water or drug during use.

The retention frame lumen 110 is loaded with the retention frame 114, which may be an elastic wire. The retention frame 114 may be configured to return spontaneously to a retention shape, such as the illustrated example "pretzel" shape or another coiled shape, such as those disclosed in the applications previously incorporated. In particular, the retention frame 114 may retain the device 100 in the body, such as in the bladder. For example, the retention frame 114 may have an elastic limit and modulus that allows the device 100 to be introduced into the body in a relatively lower-profile shape, permits the device 100 to return to the relatively expanded shape once inside the body, and impedes the device from assuming the relatively lower-profile shape within the body in response to expected forces, such as the hydrodynamic forces associated with contraction of the detrusor muscle and urination. Thus, the device 100 may be retained in the body once implanted, limiting or prevent accidental expulsion.

The material used to form the device body 106, at least in part, may be elastic or flexible to permit moving the device 100 between deployment and retention shapes. When the device is in the retention shape, the retention frame portion 104 may tend to lie inside the drug reservoir portion 102 as shown, although the retention frame portion 104 can be positioned inside, outside, above, or below the drug reservoir portion 102 in other cases.

The material used to form the device body 106 also is water permeable so that solubilizing fluid (e.g., urine or other bodily fluid) can enter the drug reservoir portion 102 to solubilize the drug units 112 once the device is implanted. For example, silicone or another biocompatible elastomeric material may be used. In other embodiments, the device body may be formed, at least in part, of a water-impermeable material.

Figure 2A:
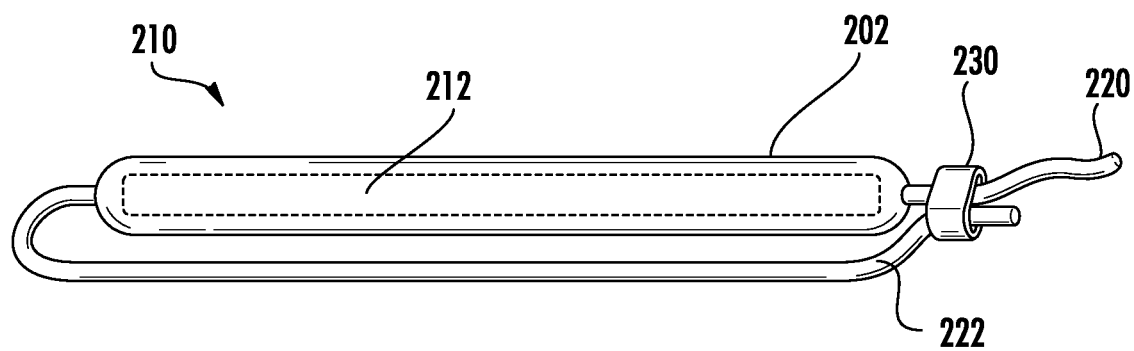
FIGS. 2A-2B illustrate another embodiment of an intravesical drug delivery device that may be used for administering trospium as described herein.
Figure 2B:
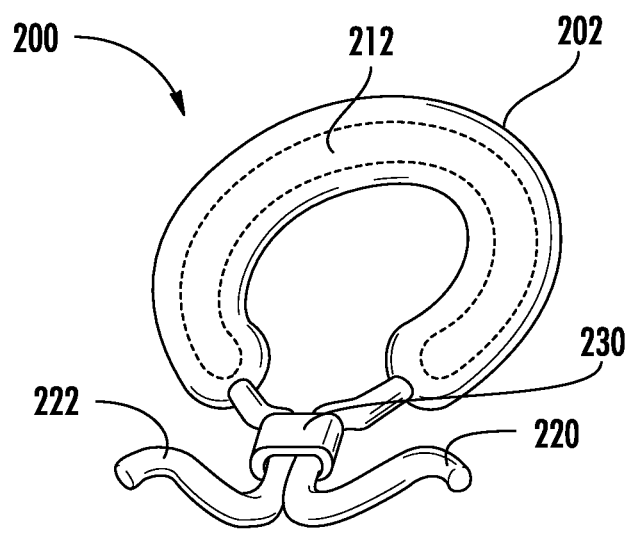

FIG. 2A illustrates an implantable drug delivery device 200, which includes a drug reservoir 202 loaded with drug 212 and the retention structure includes two filaments 220, 222 associated with a fastener 230. As shown, the drug reservoir 202 is an elongated tube that can be deformed between a relatively linear deployment shape, such as the shape shown in FIG. 2A, and a relatively circular retention shape, such as the shape shown in FIG. 2B. The drug 212 may be loaded in the tube in a flexible form, so that the drug reservoir 202 can be moved between the two shapes. For example, the drug 212 may be a number of solid drug tablets, a liquid, or a gel. The filaments 220, 222 may be attached to opposite ends of the drug reservoir 202 and joined by the fastener 230. The fastener 230 can be adjusted to adjust the position of one filament 220 with reference to the other 222, thereby adjusting the position of one end of the drug reservoir 202 with reference to the other end. The device 200 can assume the retention shape by adjusting the filaments 220, 222 to draw the ends of the drug reservoir 202 closer together, and thereafter the device 200 can be retained in the retention shape by preventing adjustment of the filaments 220, 222 with the fastener 230. In such an embodiment, the device 200 is manually adjusted into the retention shape by manually adjusting the filaments 220, 222 after the device 200 is inserted into the bladder.

In the illustrated embodiment, the fastener 230 is a cinch nut that permits shortening the portion of the filaments 220, 222 between the drug reservoir ends and the cinch nut, but prevents lengthening of these portions of the filaments 220, 222. Thus, the ends of the drug reservoir 202 can be drawn closer together by pulling one or both of the filaments 220, 222 through the cinch nut, causing the device 200 to assume the retention shape. Once the filaments 220, 222 have been so adjusted, the cinch nut prevents lengthening of the filaments 220, 222, retaining the device in the retention shape. Thus, manually adjusting the device 200 into the retention shape once implanted merely requires pulling one or both of the filaments 220, 222, although other fasteners 230 that require separate manipulation can be employed. Other fasteners may also be used.

To remove the device 200, one or both of the filaments 220, 222 may be snipped, causing the drug reservoir 202 to return to the deployment shape. Thereafter, the device 200 may be pulled through the urethra. Alternatively, all or a portion of the device 200 can be formed of a bioresorbable (e.g., biodegradable or bioerodible) material. In one case, the degradation of the device is substantial enough that it negates the need for a removal procedure, as the degradation products can be excreted. In another case, the fastener 230, filaments 220, 222, or a portion of the drug reservoir 202 is configured to degrade after a period (e.g., post drug release) to cause a break therein to release the tension holding the device 200 in the retention shape and permitting it to return to the deployment shape for retrieval through the urethra.

Another embodiment of an intravesical drug delivery device is illustrated in FIGS. 3A-3C. In this embodiment, the device includes a housing 300 having a single, continuous structure with multiple, discrete drug reservoir lumens 320 and optionally having at least one retention frame lumen 330 in which a retention frame 360 is disposed. Each drug reservoir lumen 320 has two defined openings, as shown in FIG. 3B, and is dimensioned to hold at least one solid drug unit 340. Solid drug unit 340 may be a drug tablet or capsule. In other embodiments not shown, each drug reservoir lumen has one defined opening. The housing may be formed of a flexible polymer, such as silicone. FIG. 3B is a cross-sectional view of the plane that bisects one of the drug reservoir lumens 320 of the housing shown in FIG. 3A along line 3B-3B. As shown in FIG. 3B, the monolithic housing 300 has two defined openings (350a, 350b) in its drug reservoir lumen 320 that expose both ends of the solid drug unit 340. The retention frame lumen 330, in this embodiment, is aligned parallel to the longitudinal axis of the housing and perpendicular to the drug reservoir lumen 320. FIG. 3C is a perspective view of a portion of the embodiment of the device 300 shown in FIG. 3A when the device is in its retention shape, which is taken when the retention frame 360 is disposed in the retention frame lumen 330. The drug reservoir lumens 320 and the retention frame 360 in the housing of this embodiment are oriented so that the drug reservoir lumens 320 are outside the retention frame's 360 arc. Alternatively, the housing in FIG. 3C can be rotated 180 degrees about the retention frame 360 to yield a configuration in which the drug reservoir lumens 320 are arranged within the retention frame's 360 arc. With this embodiment, the devices provide sufficient direct contact between solid drug units and with urine surrounding the device when deployed and retained in the bladder. In embodiments, release of the drug from the device is controlled by erosion of an exposed portion of the surface of a solid drug unit, such that the rate of drug release from the drug delivery device may be directly proportional to and limited by the total exposed surface area of the solid drug units.

Figure 4A:
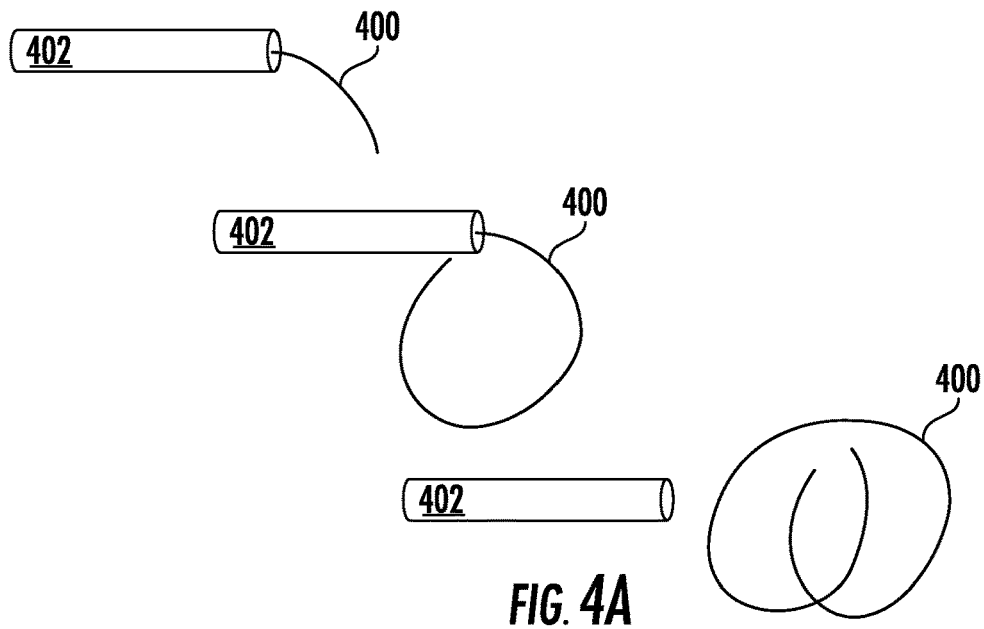
FIGS. 4A-4B illustrate a method of inserting an intravesical drug delivery device into the bladder of a patient for local administration of trospium as described herein.
Figure 4B:
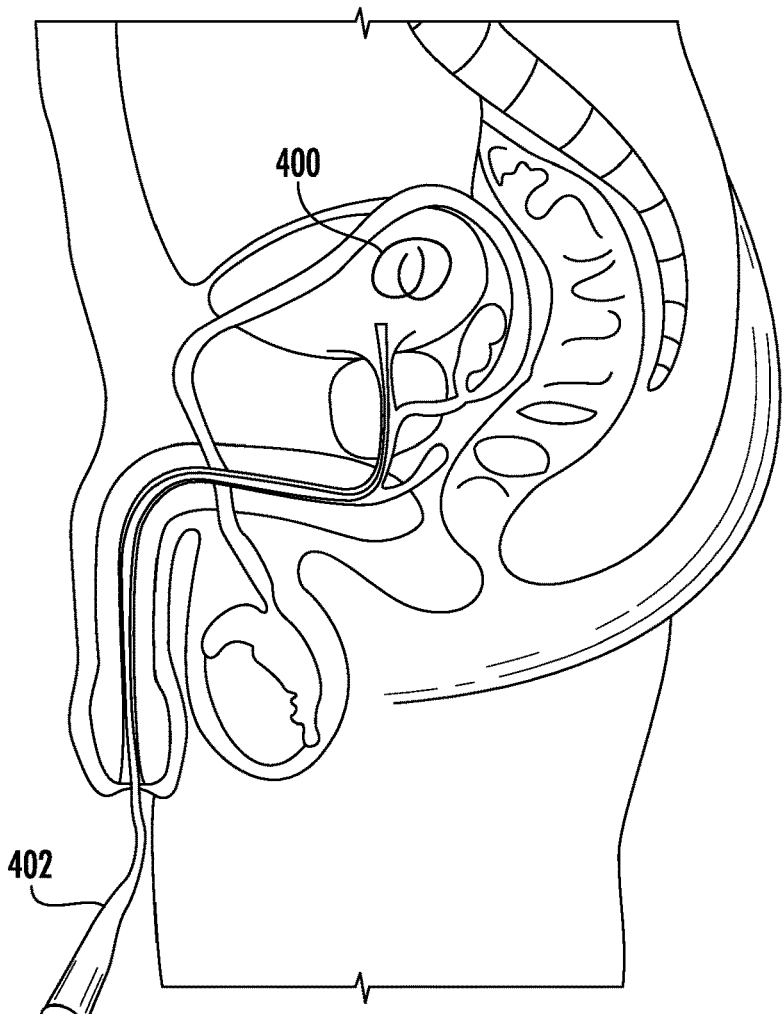

One embodiment of inserting an intravesical device 400 for subsequent controlled release of the trospium into the bladder is shown in FIGS. 4A and 4B. Here, the device 400 is shown assuming a retention shape as the device exits a deployment instrument 402. The deployment instrument 402 may be any suitable device. It may be a lumenal device, such as a catheter, urethral catheter, or cystoscope. The deployment instrument 402 may be a commercially available device or a device specially adapted for the present drug delivery devices. FIG. 4B illustrates the insertion of the device 400 into the bladder, wherein the adult male anatomy is shown by way of example. The deployment instrument 402 is inserted through the urethra to the bladder, and the device 400 may be passed from/through the deployment instrument 402, driven by a stylet or flow of lubricant or combination thereof until the device 400 exits into the bladder, and as shown is in a retention shape.

In various embodiments, the trospium may be released from the intravesical drug delivery device by diffusion to through a wall of the drug housing, by diffusion to through one or more defined apertures in a wall of the drug housing, by osmotic pressure through an aperture in the drug housing, by erosion of a drug formulation in contact with urine in the bladder, or by a combination thereof.

In embodiments in which the device comprises a drug in a solid form, elution of drug from the device occurs following dissolution of the drug within the device. Bodily fluid enters the device, contacts the drug and solubilizes the drug, and thereafter the dissolved drug diffuses from the device or flows from the device under osmotic pressure or via diffusion. For example, the drug may be solubilized upon contact with urine.

Subsequently, the device may be retrieved from the body, such as in cases in which the device is non-resorbable or otherwise needs to be removed. Retrieval devices for this purpose are known in the art or can be specially produced. The device also may be completely or partially bioresorbable, such that retrieval is unnecessary, as either the entire device is resorbed or the device sufficiently degrades for expulsion from the bladder during urination. The device may not be retrieved or resorbed until some of the drug, or preferably most or all of the drug, has been released. If needed, a new drug-loaded device may subsequently be implanted, during the same procedure as the retrieval or at a later time.

In various embodiments, the intravesical device may release trospium continuously or intermittently to achieve a concentration of trospium in the bladder that produces a sustained, therapeutically effective concentration of trospium over a period from 1 hour to 6 months, for example from 1 hour to 1 month, from 2 hours to 90 days, from 2 hours to 2 weeks, from 6 hours to 60 days, from 6 hours to 1 week, from 24 hours to 30 days, from 24 hours to 14 days, from 24 hours to 72 hours, etc. In one embodiment, the trospium is administered to the bladder for up to 180 days.

In various embodiments, trospium is administered intravesically in a dosage amount from about 0.075 mg/day to about 150 mg/day, such as from 0.15 mg/day to 15 mg/day, from 1 mg/day to 100 mg/day over the treatment period. In other embodiments, trospium is administered intravesically in a dosage amount from about 1 mg/day to about 300 mg/day, for example from 20 mg/day to 300 mg/day, from 25 mg/day to 300 mg/day, etc. over the treatment period.

In one embodiment, trospium is administered intravesically into the patient's bladder at a mean average amount of from 1 mg/day to 100 mg/day for up to 14 days. In another embodiment, trospium is administered intravesically into the patient's bladder at a mean average amount of from 1 mg/day to 100 mg/day for up to 7 days.

In another embodiment, a coating substance may be intravesically applied to the bladder wall, wherein the coating substance includes the drug and one or more excipient materials that promote adherance of the coating substance to the bladder wall and provides continuous controlled release of the drug over the treatment period. The coating substance may be a mucoadhesive formulation, such as gels, ointments, creams, films, emulsion gels, tablets, polymers, or a combination thereof. Mucoadhesive formulation polymers may include hydrogels or hydrophilic polymers, polycarbophil (i.e. Carbopols, etc.), chitosan, polyvinylpyrrolidone (PVP), lectin, polyethyleneglycolated polymers, celluloses, or a combination thereof. Suitable celluloses include methyl cellulose (MC), carboxymethyl cellulose (CMC), hydroxypropyl cellulose (HPC), or combinations thereof. The coating substance may include a permeation enhancer. Non-limiting examples of permeation enhancers include dimethyl sulfoxide (DMSO), sodium carboxymethyl cellulose (NaCMC), lipids, surfactants, or combinations thereof. In one embodiment, the coating substance may include liposomes or microparticles comprising the drug.

Figure 5A:
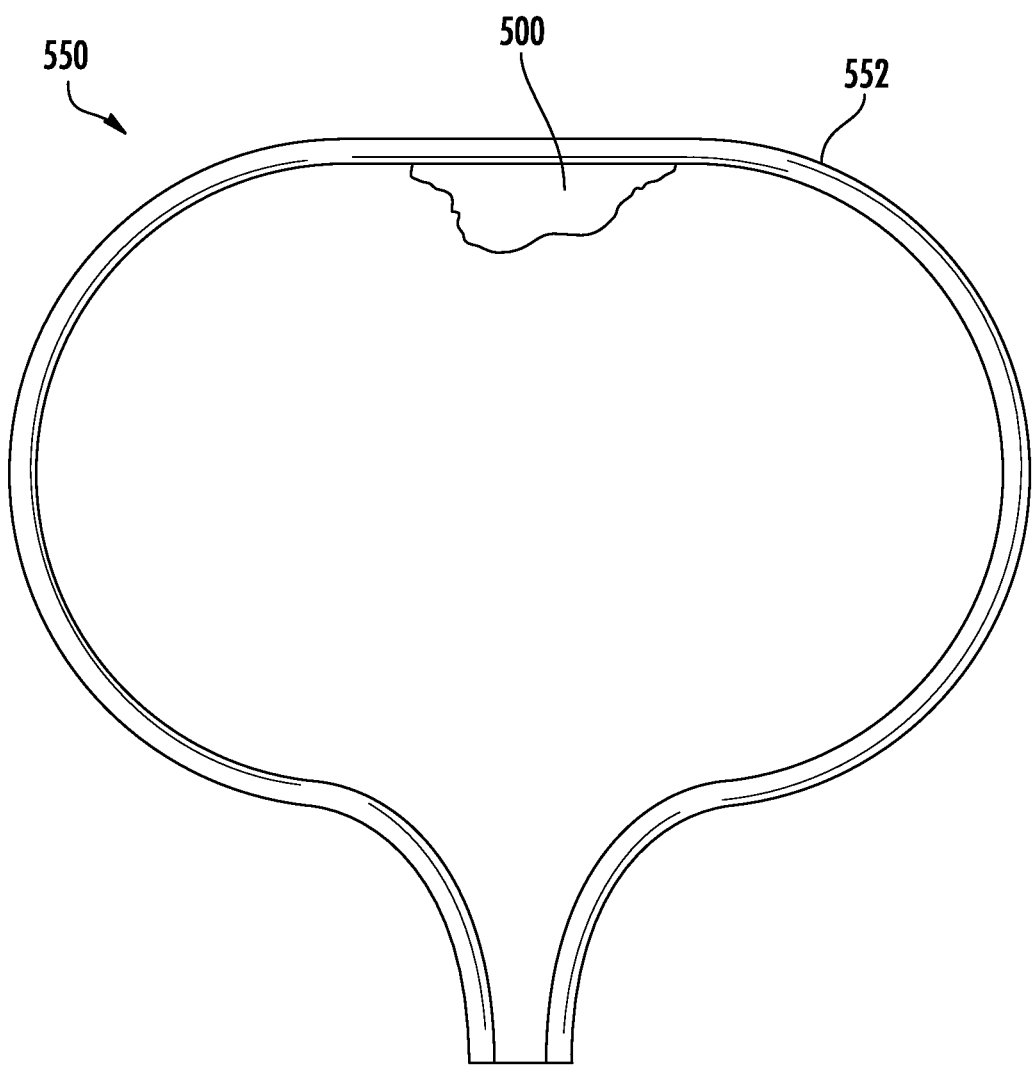
FIG. 5A illustrates a material applied to the inner surface of the bladder wall for local administration of trospium as described herein.
Figure 5B:
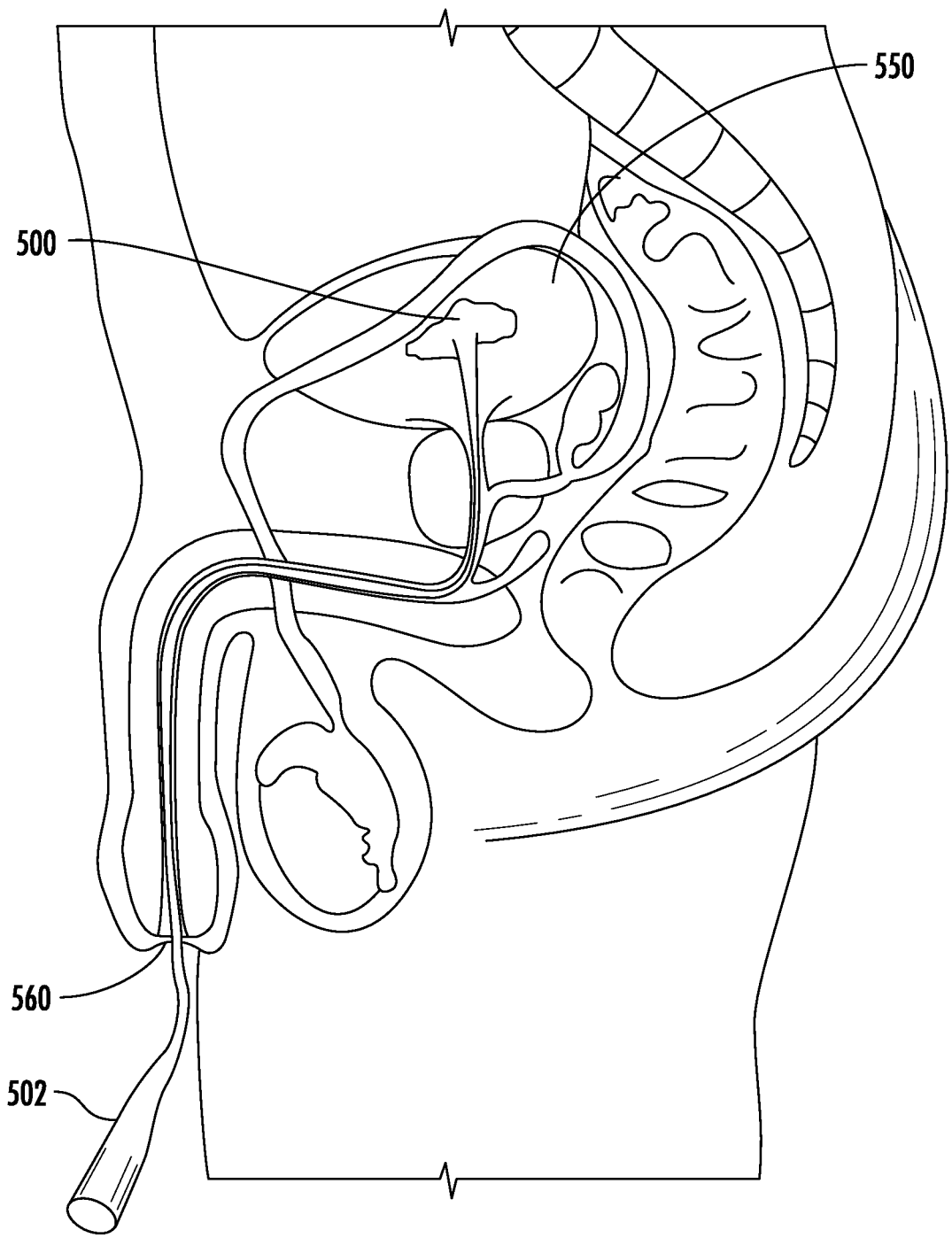
FIG. 5B illustrates a method of applying a coating material onto the inner surface of the bladder wall for local administration of trospium as described herein.
Figure 6:
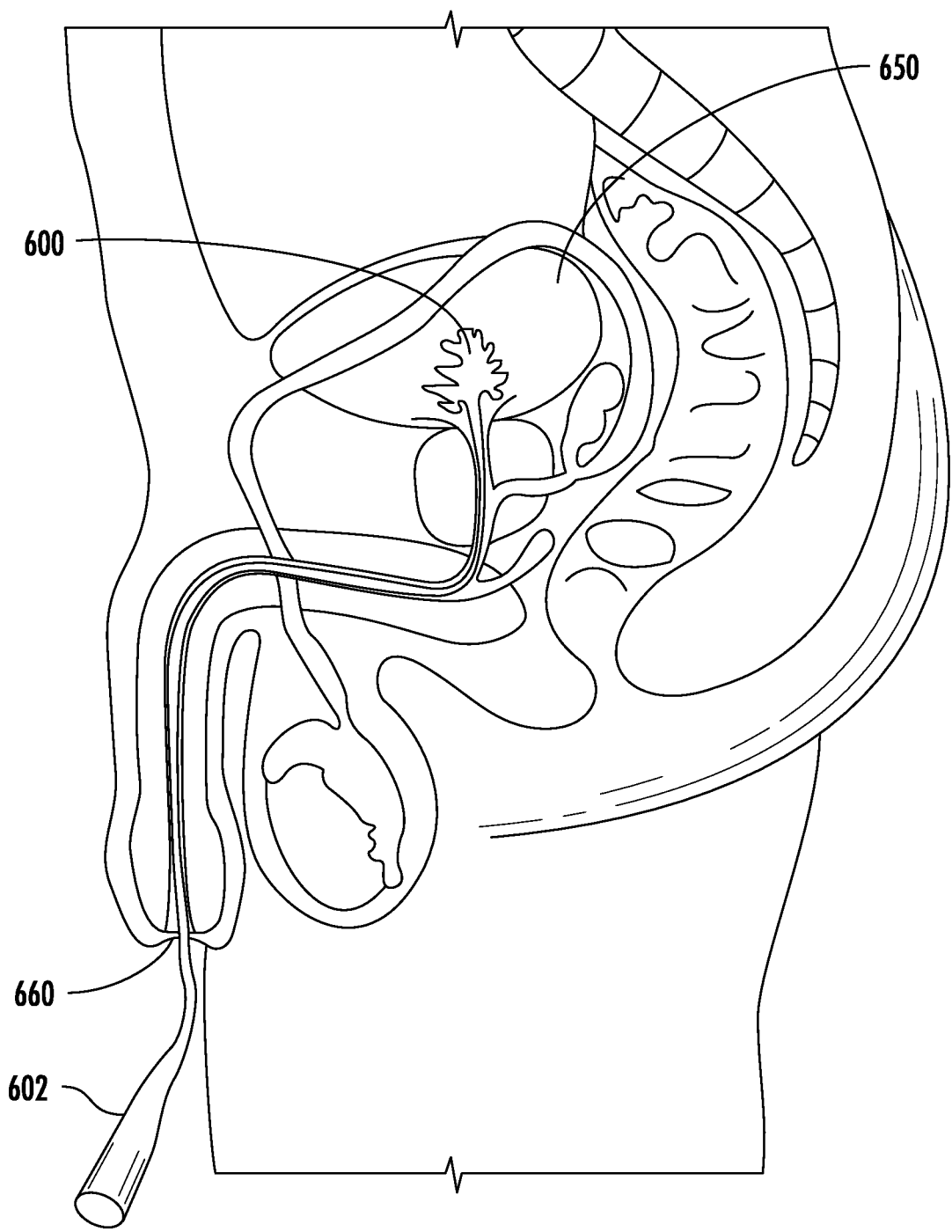
FIG. 6 illustrates a method of applying a liquid drug or drug formulation into the bladder.

As shown in FIG. 5A, a coating substance 500 may be deployed in the bladder 550 so that the coating substance 500 engages the bladder wall 552. The coating substance may be deployed in the bladder using a deployment instrument. FIG. 5B is a sagittal view of a male genitourinary system, illustrating a coating substance 500 being deployed through a deployment instrument 502 into an implantation site. By way of example, the male anatomy is shown and the implantation site is shown as the bladder 550. The coating substance 500 may be an embodiment of one of the coating substances described herein. The deployment instrument 502 may be any device designed to navigate natural lumens of the body to reach the intended implantation site. For deployment in the bladder 550, the deployment instrument 502 is sized and shaped for passing through a urethra 560 of a patient to a bladder 550 as shown. The deployment instrument 502 may be a known device, such as a catheter or cystoscope, or a custom device. The deployment instrument 502 is used to deploy the coating substance 500 into the body and is subsequently removed from the body, leaving the coating substance 500 wholly implanted in the body. Once so implanted, the coating substance 500 may release drug into the body for an extended period. A comparable procedure can be used to deploy any of the devices or drugs described herein into other parts of the body through other natural lumens. For example, as shown in FIG. 6, a deployment instrument 602 can be used to deploy a liquid drug or drug formulation 600 into the bladder 650 by passing the deployment instrument 602 through a urethra 660.

In one embodiment, the coating substance is applied intravesically in combination with an intravesical delivery device. For example, trospium may be administered to the bladder both from the coating substance and from the delivery device. In one embodiment, the coating substance provides release of trospium over a first portion of a treatment period and the delivery device provides release of trospium over a second portion of the treatment period. Such an embodiment may beneficially work better than either alone, in that the coating substance may provide a more immediate delivery of therapeutic levels, while the device may undergo an induction period (e.g., time for water to be imbibed by the device and dissolve drug housed therein) before releasing therapeutic levels of the drug. The first and second portions may overlap.

In various embodiments, a second therapeutic agent is administered to the patient. The second therapeutic agent may be administered intravesically, orally, or by other routes of administration. For example, the second therapeutic agent may include gemcitabine or another cytotoxic agent, an analgesic agent, an anti-inflammatory agent, or a combination thereof. The second therapeutic agent may be selected for treatment of OAB or non-OAB indications. In one embodiment, the second therapeutic agent prevents, treats, or ameliorates cystitis of the bladder. In other embodiments, the second therapeutic agent prevents, treats, or ameliorates bladder cancer or infections of the bladder.

In one embodiment, a first therapeutic agent is administered via a coating substance and a second therapeutic agent is administered by an intravesical drug delivery device. The first and second therapeutic agents may be the same pharmaceutically active agent or different pharmaceutically active agents. In an embodiment, the first and/or second therapeutic agent includes trospium.

The term "patient" as used herein refers to humans or other mammals, such as in veterinary or livestock applications. In a particular embodiment, the patient is an adult human.

The present invention may be further understood with reference to the following non-limiting examples.

EXAMPLE 1

Antimuscarinic Screen in Rat Bladder Perfusion Model

A study was conducted to intravesically perfuse oxybutynin chloride, tolterodine tartrate, or trospium chloride into rats fitted with indwelling bladder and jugular cannulas. The rats were fully mobile post-surgery.

The drugs were perfused at varying rates, concentrations, and times. Serial blood and urine samples were taken, and tissues (bladder, ureter, kidney, and prostate) were sampled to determine drug levels and distribution. Tissue histological exams were completed for safety.

As demonstrated by Table 1, the results indicated that oxybutynin exhibited significantly higher systemic absorption following intravesical administration than either tolterodine or trospium.

TABLE 1

Antimuscarinic Screen - Plasma Levels

| Drug | Urine to Plasma Ratio | Effective Urine Concentration (µg/mL) | Est $C_{max}$ (ng/mL) |
|---|---|---|---|
| Oxybutynin | 2,130 | 1 to 10 | 0.4 to 4.6 |
| Trospium | 15,380 | 1 to 10 | 0.06 to 0.7 |
| Tolterodine | 31,190 | 1 to 10 | 0.03 to 0.3 |

Consistent with higher systemic exposure, oxybutynin exhibited a low total recovery. Specifically, the estimated intravesical absorption of oxybutynin was 83% of the intravesical dose. The urine concentration (µg/mL) of oxybutynin was less than 100 from 0-24 hours after exposure and less than 50 from 24-48 hours and 48-72 hours after exposure. In contrast, the recovery of trospium and tolterodine was near the theoretical dose (3.3 mg/day). The urine concentration (µg/mL) of trospium in the urine was more than 200 from 0-24 hours after exposure, about 150 from 24-48 hours after exposure, and more 125 from 48-72 hours after exposure. The urine concentration (µg/mL) of tolteridine in the urine was more than 200 from 0-24 hours after exposure and more than 150 from 24-48 hours and 48-72 hours after exposure.

These results showed stable levels over 72 hours and no adverse effects on the urothelium.

EXAMPLE 2

Intravesical Pharmacology Screen in Rat Bladder Perfusion Model

Carotid artery and bladder catheterized rats were intravesically perfused with oxybutynin chloride, tolterodine tartrate, or trospium chloride at varying dosages of escalating concentrations with acetic acid. Intercontraction intervals and intravesical pressure were measured during a control periods and treatment periods.

The rats' bladder catheters were connected to a pressure transducer and syringe-pump to allow perfusion. The bladders were perfused (50 µL/minute) with saline for one hour to obtain stable micturition cycles. The perfusion then was switched to a weak acidic solution sufficient to stimulate the noxious receptors in the urothelium without inducing structural or metabolic damage to the tissue. The acidic solution was comprised of 0.5% acetic acid exhibiting an average pH of approximately 3.5. A 45 minute baseline was recorded.

The vehicle or antimuscarinic drugs were administered intravesically at escalating concentrations (see Table 2 for drugs and concentrations used) with acetic acid instillation (50 µL/minute). Each dose was administered for a 30-minute period. The intravesical pressure and intercontraction interval was recorded during the last 30 minutes of the control period (baseline) and during the 30 minutes of each treatment period, with one treatment period corresponding to one dose of drug.

The active doses ranged between 0.1 µg/mL to 100 µg/mL. The target intravesical doses were estimated to be 0.1 to 1 µg/mL (0.2 to 1.5 mg/day). The dosages that were used are shown in Table 2.

TABLE 2

Dosages of Antimuscarinics

| | Treatment | | | | |
|---|---|---|---|---|---|
| | Dose 1 (D1) (µg/mL) | Dose 2 (D2) (µg/mL) | Dose 3 (D3) (µg/mL) | Dose 4 (D4) (µg/mL) | Dose 5 (D5) (µg/mL) |
| Vehicle (saline) | Corresponds to an intravesical instillation of acetic acid (0.5%) | | | | |
| Oxybutynin hydrochloride (OXB) | 0.05 | 0.1 | 1 | 10 | 100 |
| Trospium chloride (TC) | 0.05 | 0.1 | 1 | 10 | 100 |
| Tolterodine tartrate (TT) | 0.05 | 0.1 | 1 | 10 | 100 |

Figure 7D:
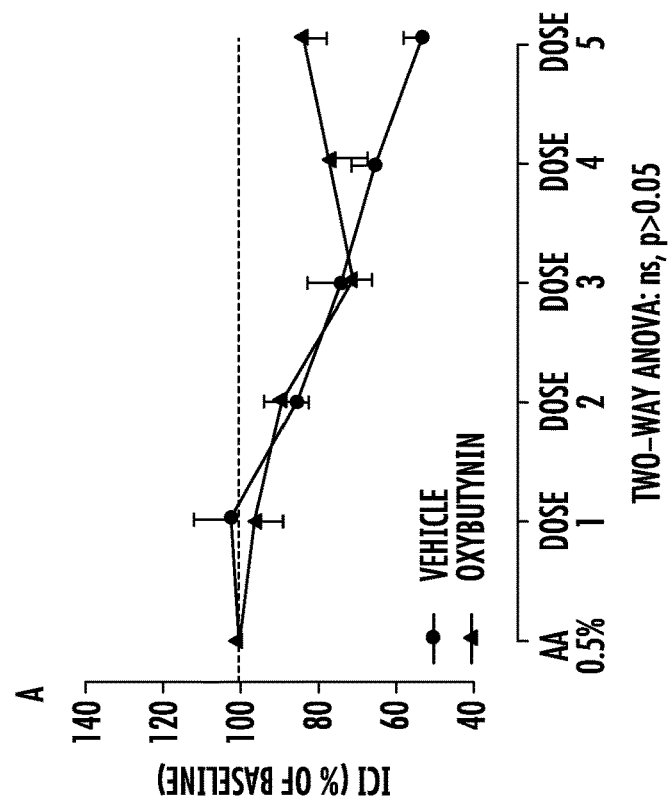
Figure 7C:
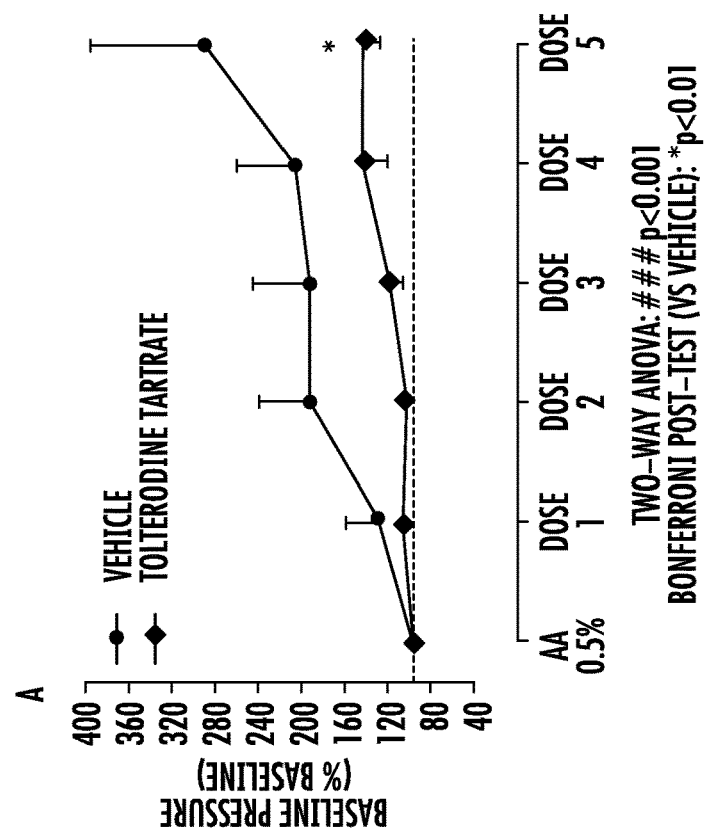
Figure 7F:
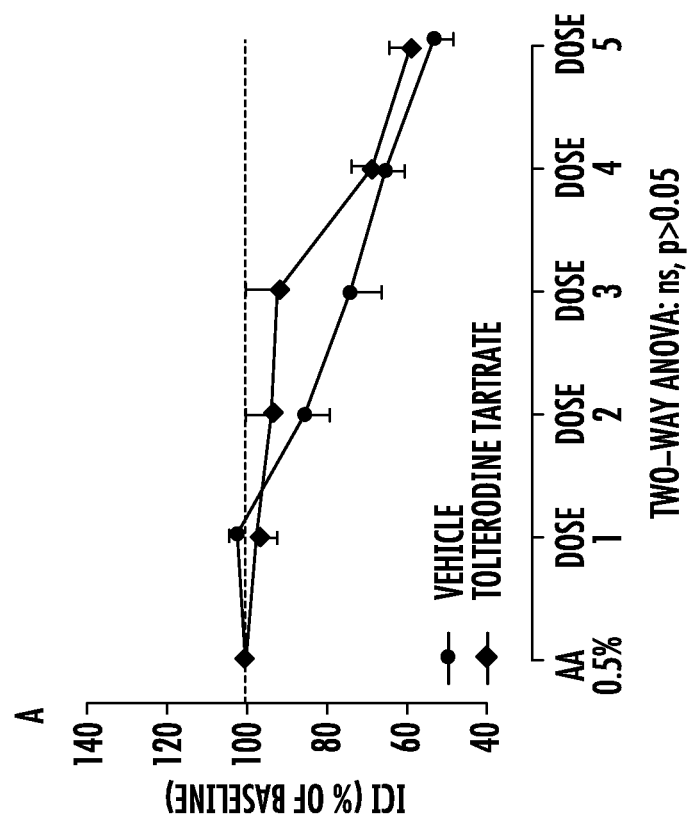
Figure 7E:
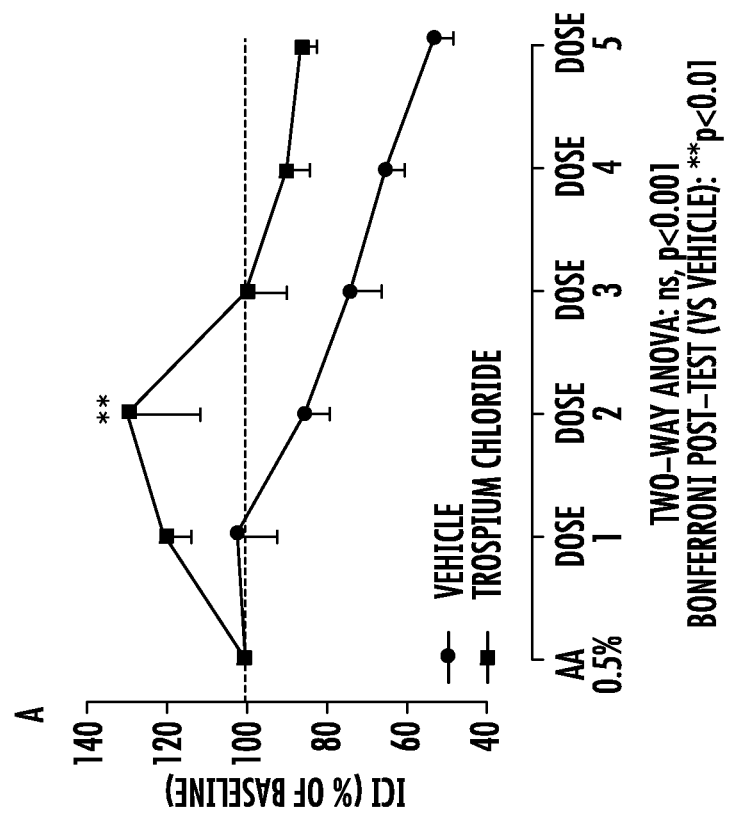

As shown in FIGS. 7A-7C, the results indicate that administration of oxybutynin, trospium, and tolterodine each produced dose dependent reductions in acetic acid induced increased intravesical pressure. Unexpectedly however, trospium was unique compared to oxybutynin and tolterodine, because it increased the inter-contraction intervals compared to the control. As shown in FIGS. 7D-7F, oxybutynin hydrochloride (FIG. 7D) and tolterodine tartrate (FIG. 7F) had little effect on the intercontraction intervals compared to the control, but trospium chloride (FIG. 7E) kept the inter-contraction intervals closer to the baseline measurement. Thus trospium may exhibit greater potential to reduce bladder spasms and involuntary detrusor contractions without suppressing overall bladder function.

The data showed activity over the range of 0.05 to 100 µg/mL, assuming an average urine output of 1500 mL/day. Based on this observation, suitable intravesical dosages of trospium may range from about 0.075 mg/day to about 150 mg/day for up to 180 days. The high dose of 150 mg generally would not be intended to last 180 days but could be used for more acute applications.

EXAMPLE 3

Extended Release of Trospium from Device

An in vitro study was done to show zero order release of trospium chloride over an extended period. A silicone tube device housing was used, with each device loaded with an average of about 77 mg of trospium chloride. The silicone tube ID was 1.5 mm. For Group 1 (N=3), the silicone tube wall was 0.2 mm thick, and for Group 2 (N=3), the silicone tube wall was 0.8 mm. The ends of the loaded silicone tube were sealed, with each device having a release orifice located at one end of the tubing. The orifice diameter for all devices was 0.28 mm. The trospium chloride was in the form of tablets, wherein the length of the tablets was approximately 3.8 cm, with the tablets having the formulation of 90% trospium chloride (TrosCl), 5% PVP, and 5% PEG 8k.

Each drug-loaded device was placed in release media, which was 40 mL of aqueous 150 mM acetate buffer with pH 4.5. Over time, the release media was imbibed by the silicone tubing and dissolved the tablets, such that solubilized drug was released through the orifice. The release media was periodically sampled and the amount of trospium in the release media was measured. The study was stopped after 50 days, although the device would have continued to release drug for a longer period if permitted.

The results are shown in Table 3 below. The thicker wall (Group 2) device provided slower release than the thinner wall (Group 1), however both devices provided zero order, continuous release of therapeutically effective amounts of trospium chloride for at least 50 days.

TABLE 3

Cumulative Trospium Chloride Released
Cumulative Trospium Chloride Released (mg)

| Elapsed Time (days) | Group 1 | | Group 2 | |
|---|---|---|---|---|
| | Mean | SD | Mean | SD |
| 1 | 1.36 | 0.04 | 0.53 | 0.44 |
| 2 | 2.91 | 0.02 | 1.86 | 0.46 |
| 3 | 4.75 | 0.09 | 2.75 | 0.55 |
| 6 | 10.99 | 0.22 | 4.81 | 0.67 |
| 8 | 15.25 | 0.26 | 6.13 | 0.72 |
| 10 | 19.58 | 0.25 | 7.46 | 0.78 |
| 13 | 25.62 | 0.32 | 9.68 | 0.84 |
| 16 | 30.26 | 0.38 | 12.83 | 0.90 |
| 22 | 32.88 | 0.54 | 16.16 | 0.96 |
| 36 | 39.34 | 0.61 | 26.09 | 0.90 |
| 50 | 46.44 | 0.57 | 33.98 | 1.00 |

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

I claim:

1. A method of administering trospium to a patient in need of treatment of overactive bladder, the method comprising:
    locally administering trospium into the bladder of a patient to achieve a sustained concentration of trospium in urine in the bladder sufficient to produce a therapeutic concentration of trospium in bladder tissue over a treatment period from 1 week to 6 months,
    wherein the locally administering into the patient's bladder is from an intravesical drug delivery device which continuously releases the trospium into the urine in the bladder at a mean average amount of from 0.15 mg/day to about 15 mg/day over the treatment period,
    wherein the sustained concentration of trospium in urine in the bladder is from 0.05 µg/ml to 100 µg/ml continuously over the treatment period.

2. The method of claim 1, wherein the trospium is released from the intravesical drug delivery device by diffusion to through a wall of the device, by diffusion to through one or more defined apertures in a wall of the device, by osmotic pressure through an aperture in the device, or a combination thereof.

3. The method of claim 1, further comprising administering a second therapeutic agent to the patient.

4. The method of claim 3, wherein the second therapeutic agent is administered intravesically.

5. The method of claim 1, wherein the sustained concentration of trospium in urine in the bladder is from 0.1 µg/ml to 100 µg/ml continuously over the treatment period.

6. The method of claim 1, wherein the sustained concentration of trospium in urine in the bladder is from 10 µg/ml to 100 µg/ml continuously over the treatment period.

7. The method of claim 1, wherein the sustained concentration of trospium in urine in the bladder is from 1 µg/ml to 10 µg/ml continuously over the treatment period.

* * * * *